United States Patent [19]
Varsseveld

[11] Patent Number: 6,068,641
[45] Date of Patent: May 30, 2000

[54] IRRIGATED BURR

[75] Inventor: Cris Van Varsseveld, Olsdmar, Fla.

[73] Assignee: Linvatec Corporation, Largo, Fla.

[21] Appl. No.: 09/140,123

[22] Filed: Aug. 25, 1998

Related U.S. Application Data

[60] Provisional application No. 60/057,976, Sep. 4, 1997.

[51] Int. Cl.$^7$ ..................................................... A61B 17/32
[52] U.S. Cl. ............................................................... 606/170
[58] Field of Search .................................. 606/170, 180, 606/80

[56] References Cited

U.S. PATENT DOCUMENTS

| | | |
|---|---|---|
| 2,243,299 | 5/1941 | Travers . |
| 2,721,555 | 10/1955 | Jenney . |
| 3,294,085 | 12/1966 | Wallace . |
| 3,835,842 | 9/1974 | Iglesias . |
| 3,844,272 | 10/1974 | Banko . |
| 3,850,162 | 11/1974 | Iglesias . |
| 3,850,175 | 11/1974 | Iglesias . |
| 3,882,872 | 5/1975 | Douvas et al. . |
| 3,900,022 | 8/1975 | Widran . |
| 3,996,935 | 12/1976 | Banko . |
| 4,167,943 | 9/1979 | Banko . |
| 4,301,802 | 11/1981 | Poler . |
| 4,517,977 | 5/1985 | Frost . |
| 4,643,717 | 2/1987 | Cook et al. . |
| 4,650,461 | 3/1987 | Woods . |
| 4,674,502 | 6/1987 | Imonti . |
| 4,715,848 | 12/1987 | Beroza . |
| 4,750,488 | 6/1988 | Wuchinich et al. . |
| 4,844,088 | 7/1989 | Kambin . |
| 4,955,882 | 9/1990 | Hakky . |
| 5,019,036 | 5/1991 | Stahl . |
| 5,163,433 | 11/1992 | Kagawa et al. . |
| 5,190,541 | 3/1993 | Abele et al. . |
| 5,217,479 | 6/1993 | Shuler . |
| 5,244,462 | 9/1993 | Delahuerga et al. . |
| 5,269,785 | 12/1993 | Bonutti ..................................... 606/80 |
| 5,300,069 | 4/1994 | Hunsberger et al. . |
| 5,354,291 | 10/1994 | Bales et al. . |
| 5,403,276 | 4/1995 | Schechter et al. . |
| 5,403,317 | 4/1995 | Bonutti . |
| 5,405,348 | 4/1995 | Anspach, Jr. et al. . |
| 5,505,210 | 4/1996 | Clement . |
| 5,624,393 | 4/1997 | Diamond . |
| 5,685,838 | 11/1997 | Peters et al. . |
| 5,759,185 | 6/1998 | Grinberg ..................................... 606/80 |

FOREIGN PATENT DOCUMENTS

| | | |
|---|---|---|
| 0 240 457 | 3/1987 | European Pat. Off. . |
| 2 267 828 | 12/1993 | United Kingdom . |

OTHER PUBLICATIONS

Article entitled "Stop Clogging in Your Sinus Cases—Put Our Typhoon Irrigated Cutter Blade in Your Handpiece", Trebay Medical Corp.2 pages.

ENT Ear Nose & Throat Journal, "The Next Generation Is Here—Introducing Hummer 2 ENT Micro Debrider", Jan. 1996 vol. 75 No. 1, 2 pages.

*Primary Examiner*—Michael Buiz
*Assistant Examiner*—Vy Q. Bui
*Attorney, Agent, or Firm*—Gene Warzecha

[57] ABSTRACT

A rotatable shaver in the form of an endoscopic burr instrument suitable for use at a non-fluid filled surgical site. The burr instrument comprises an elongated tubular outer member and an elongated tubular inner member rotatably situated within the outer member. A burr or other abrading tool is secured to the distal end of the inner member and abraded tissue and other debris is or may be aspirated through the lumen of the inner member. A fluid inlet port in the outer member provides irrigating fluid to the proximal end of the outer member and the fluid is conveyed to one or more longitudinally extending fluid channels between the inner and outer members. The channel or channels direct the fluid distally from an outlet port at the distal tip of the outer member in order to irrigate the surgical site. In order to prevent irrigating fluid from being directly aspirated, a barrier is provided to separate the burr tip and the outlet port from the entrance to the lumen of the inner member.

9 Claims, 7 Drawing Sheets

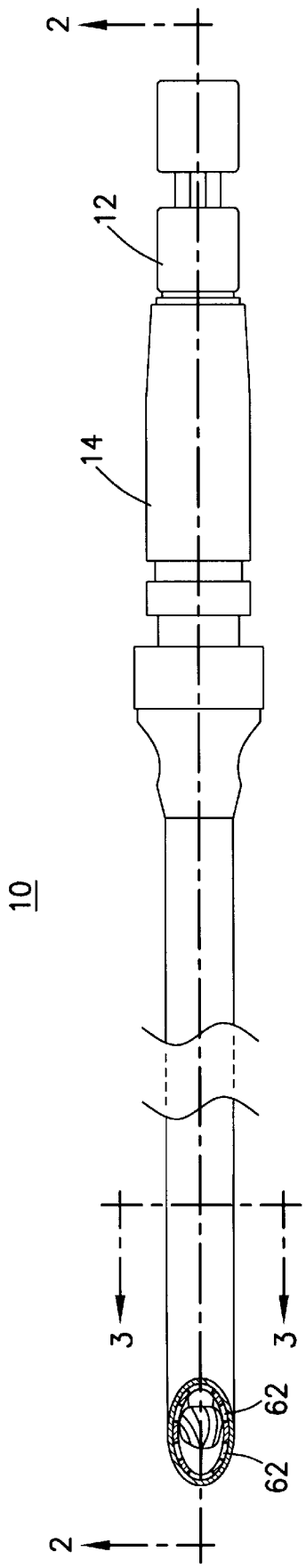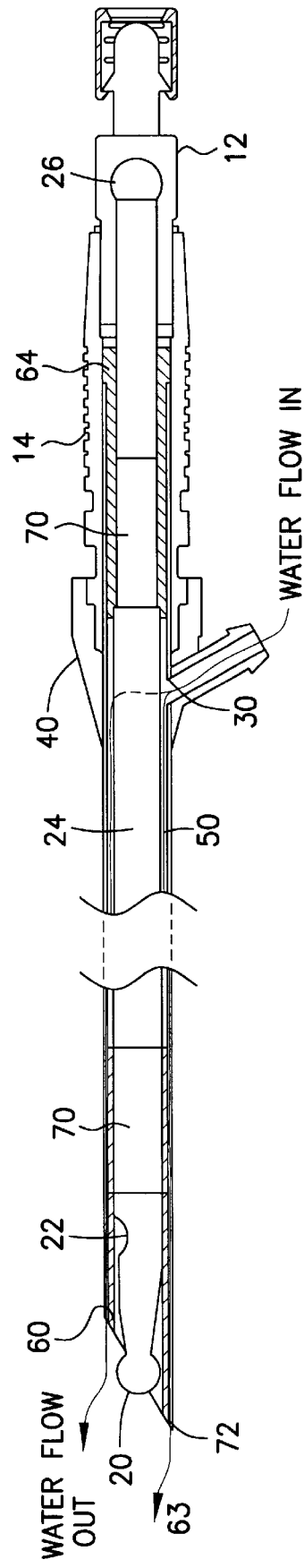

SECTIONS B—B

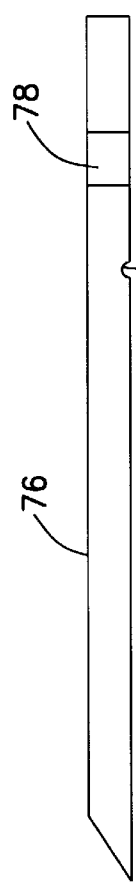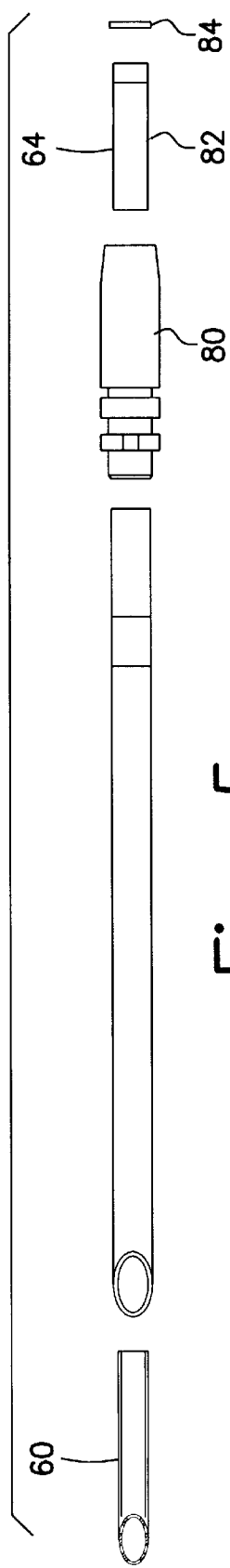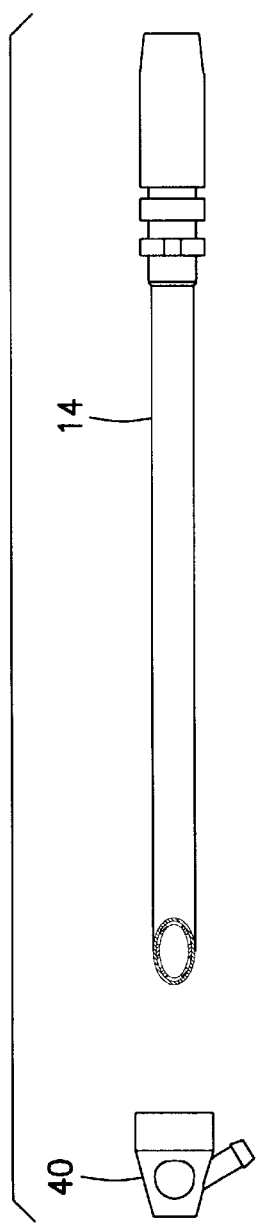
Fig. 4
Fig. 5
Fig. 6

IRRIGATED BURR

This application claims benefit to U.S. provisional application No. 60/057,926 filed Sep. 4, 1997.

BACKGROUND OF THE INVENTION

1. Field of the Invention

The invention relates generally to powered endoscopic cutting devices. More particularly, the invention relates to rotating shaver systems for use in various endoscopic surgical procedures. Still more particularly, the invention relates to rotating burrs and their method of use in endoscopic surgical procedures at non-fluid filled surgical work sites.

2. Description of the Prior Art

The use of elongated surgical cutting instruments has become well accepted in performing closed surgery such as arthroscopic or, more generally, endoscopic surgery. In closed surgery, access to the surgical site is gained via one or more portals, and instruments and scopes used in the surgical procedure must be elongated to permit the distal ends of the instruments and cameras to reach the surgical site. Some conventional surgical cutting instruments (shavers) for use in closed surgery are rotary powered and have a straight, elongated outer tubular member and a straight, elongated inner tubular member concentrically disposed in the outer tubular member. The inner and outer members both separately and jointly are sometimes referred to in the art as "blades" and are usually disposable. The outer member has a distal end having an opening in the end or side wall (or both) to form a cutting port or window and the inner member has a distal end disposed adjacent the opening in the distal end of the outer member. The inner member is (usually) easily insertable into and removable from the outer member to facilitate cleaning or interchanging parts. Each of the elongated members has a hub or termination at its proximal end in order to attach the components to a rotary drive means within a reusable handpiece. The distal end of the inner tubular member has a cutting means or cutting edge for engaging tissue via the opening in the distal end of the outer tubular member. In many cases (but not all) this distal cutting means cooperates with the opening in the outer member to shear, cut or trim tissue. In some cases, such as burrs, the opening in the outer member merely allows access to the tissue and does not otherwise cooperate with the cutting means. The term "cutting edge" or "cutting means" as used herein is intended to include abrading (e.g. burrs) and other devices whether or not there is any traditional cutting or shaving action and whether or not there is any cooperative shearing action. The inner tubular member is rotatably driven about its axis from its proximal end, normally via a handpiece having a small electric motor which is controlled by either finger actuated switches on the handpiece, a foot switch or switches on a console supplying power to the handpiece. The distal end of the various styles of inner tubular members can have various configurations depending upon the surgical procedure to be performed, and the opening in the distal end of the outer tubular member would then have a configuration adapted to cooperate with the particular configuration of the distal end on the inner tubular member. For example, the inner and outer tubular members can be configured to produce whisker cutting, synovial resection, arthroplasty burring or abrading, side cutting, meniscus cutting, trimming, full radius resection, end cutting and the like, and the various configurations are referred to generally as cutting means.

The aforementioned elongated surgical cutting instruments have also been produced in angled configurations in which the axes of the distal tips of the inner and outer members are aligned and offset or bent at a fixed angle relative to the axes of the proximal ends of the aligned inner and outer members. Examples of such fixed-angle, rotary surgical instruments are shown in U.S. Pat. No. 4,646,738 (Trott), assigned to the assignee hereof, and in European Patent Application 0 445 918 (Krause et al.). In other respects the operation of these fixed-angle shavers is largely the same as that of the straight shavers described above. Known fixed-angle shavers are generally produced with only one degree of bend—usually 15°. Recently a variable-angle (i.e. bendable) rotary shaver system has been introduced and is described in U.S. Pat. No. 5,411,514 (Fucci et al.), assigned to the assignee hereof, in which the outer tube may be bent by a user to a user-selected angle while still enabling the inner tube to be selectively inserted into and removed from the outer tube. The inner member of this device has a hollow plastic body and a metallic distal tip into which a cutting edge is formed. In all of these devices, the loose tissue resulting from the cutting, resecting or abrading procedure may be aspirated through the hollow lumen of the inner tubular member to be collected via a vacuum tube communicating with the handpiece. The devices are generally used in an aspiration-only mode since the surgical site is usually distended by some fluid medium.

However, during certain surgical procedures there is no fluid medium surrounding the work site and it is desirable to introduce irrigating fluid to the surgical site in order to simply irrigate the site to improve visualization or to facilitate the aspiration of debris. Such irrigation is usually provided by separate instruments generally known as irrigation/aspiration devices which can be used to either irrigate or aspirate a site. Recently, powered endoscopic surgical cutting devices have been produced in order to simultaneously provide irrigation and aspiration without the necessity of using a separate instrument.

One known device described in U.S. Pat. No. 5,782,795 (Bays) comprises a rotating shaver blade having a separate fluid tube secured to the outside of the outer tubular member. The proximal end of the tube is connected to a source of fluid supply and the distal end of the tube is joined to a fluid port formed in the distal end of the outer tubular member. Fluid is cyclically permitted to flow into the inner tubular member when the inner cutting window faces the fluid port.

Another known irrigating shaver blade assembly utilizes a dual-lumen plug to connect a rotating shaver blade to a fluid source. One lumen of the plug permits fluid to flow into the space between the inner and outer tubular members and the other lumen permits aspiration through the lumen of the inner member.

Another known irrigating shaver blade assembly described in a co-pending application assigned to the assignee hereof and incorporated by reference herein, comprises a shaver blade assembly in which the outer tubular member is provided with a fluid inlet port which is selectively engageable with a fluid adapter. The fluid adapter can communicate irrigating fluid from a fluid source through the fluid inlet port and an elongated channel between the inner and outer tubular members.

None of the known irrigating shaver blade assemblies is provided with a burr at the distal tip of the inner member. In non-fluid filled surgical work sites the use of a burr against hard tissue such as bone tends to create bone dust and other tissue debris which can obscure visualization of the work site through an associated endoscope.

It is accordingly an object of this invention to produce a rotating shaver assembly having a burr at the distal end of the inner member and fluid channel means for communicating irrigating fluid to the distal end of the device.

It is also an object of this invention to produce such an irrigated burr without increasing the diameter of the outer member of the shaver assembly by utilizing an external fluid conduit.

SUMMARY OF THE INVENTION

These and other objects of the invention are achieved by the preferred embodiment disclosed herein which is an irrigatable surgical instrument comprising an elongated tubular outer member and an elongated tubular inner member rotatably situated within the outer member. A tissue cutting means such as a burr is adjacent an axially aligned opening on the inner member and tissue/debris at the surgical site is aspirated through a lumen within the inner member. A fluid inlet port in the outer member directs fluid toward its distal end and channel means at the distal end receives fluid from the fluid inlet port and conveys it to one or more outlet ports at the tip of the outer member. The channel means comprises at least one longitudinally aligned channel and may comprise a plurality of annularly spaced longitudinal channels.

The invention also resides in the method of resecting tissue at a non-fluid filled surgical site. The method comprises the steps of providing an elongated powered cutting instrument having a proximal end, a distal end, a fluid inlet port at the proximal end and an aspiration port at the distal end, and further providing the instrument with a fluid outlet port adapted to direct fluid distally. The method further comprises the step of resecting tissue while directing fluid from the fluid outlet port.

BRIEF DESCRIPTION OF THE DRAWINGS

FIG. 1 is a top plan view of an irrigated burr assembly constructed in accordance with the principles of this invention.

FIG. 2 is a cross-sectional view of FIG. 1 taken along the line A—A.

FIG. 4 is a cross-sectional view of the tube portion of the outer tubular member of the burr assembly of FIG. 1.

FIG. 5 is an expanded view of the outer tubular member.

FIG. 6 is an assembled top plan of the outer tubular member showing a selectively attachable fluid adapter designed to fit over the outer tube to provide fluid from an external source to the fluid inlet port in the outer tube.

DESCRIPTION OF THE PREFERRED EMBODIMENT

Figure 3A:
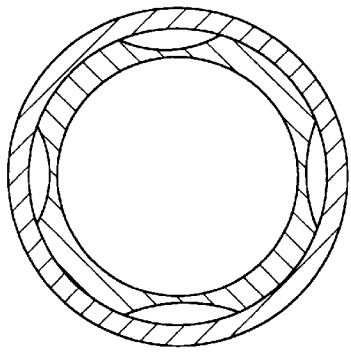
FIG. 3 is a series of possible alternative cross-sectional views taken along the line B—B of FIG. 1.
Figure 3B:
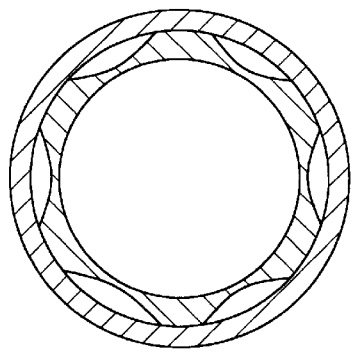
Figure 3C:
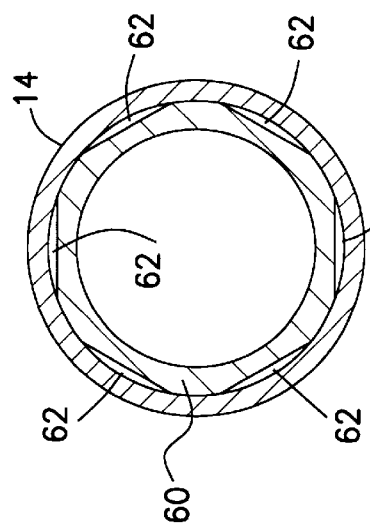
Figure 3D:
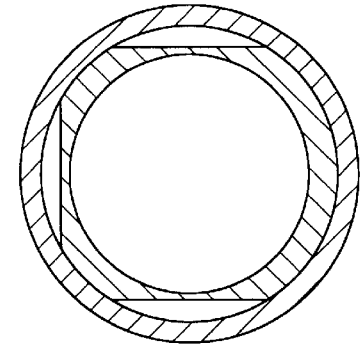
Figure 3E:
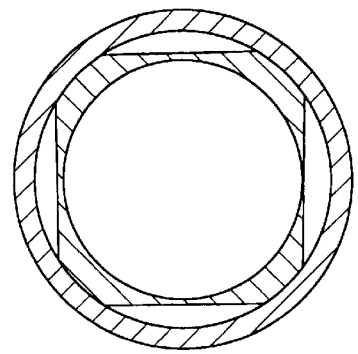
Figure 3F:
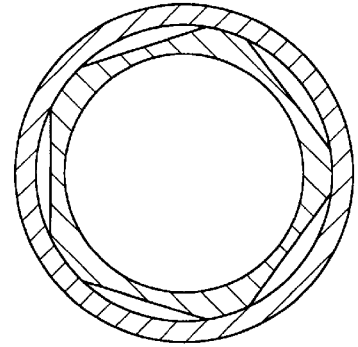
Figure 3G:
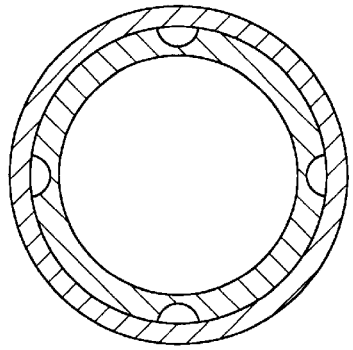

As shown in the Figures, the invention is an irrigated burr 10 for use with a surgical rotatable shaver system. The irrigated burr 10 comprises an elongated tubular inner member 12 which has a distal end and a proximal end and is rotatably situated in axial alignment within a stationary elongated tubular outer member 14. The inner and outer tubular members may be either straight, bent or bendable and are assembled and attached to a handpiece (not shown) for rotatably turning the inner member.

The distal tip of the inner member is provided with a cutting element or burr 20 having a proximal end and a distal end, and an aperture 22 for providing access to the interior lumen 24 of the inner member. The burr assembly is operated under suction so that fluid and tissue debris may be drawn proximally through the aspiration aperture 22 at the distal tip of the inner member, through the lumen 24 of the inner member and out an aperture 26 at the proximal end of the inner member. The device is provided with a fluid inflow port 30 in the outer surface of the outer tubular member 14 and an adapter 40 is utilized to connect this fluid inlet via tubing to a source of irrigating fluid (not shown). Irrigating fluid is passed through a channel or annular space 50 between the inner and outer members 12, 14 toward the burr tip 20. At the distal end of the device the annular space 50 between the inner and outer members is blocked by a tubular insert 60 having a series of circumferentially arranged longitudinally extending distal channel sections 62 which serve to guide the irrigating fluid from the annular space 50 toward the distal tip of the device. In the preferred embodiment the plurality of circumferentially arranged distal channel sections may be created by a cylindrical tubular insert having a predetermined length and secured within the interior of the outer member near its distal end. The distal end of the insert may be shaped to conform to the distal end of the outer member. As shown in the Figures, the angled distal tip of the outer member results in the distal-most end of some channel sections 62 being situated distally of the proximal end of the cutting element itself. The axis of the insert 60 is aligned with the axes of the inner and outer members. The cylindrical insert has a plurality of flats or grooves formed in its exterior surface so that a plurality of distal channels 62 are formed between the cylindrical insert and the inner surface of the outer tubular member 14. It will be understood that the annular space 50 between the fluid port 30 at the proximal end of the outer member and the distal tip is effectively blocked by this cylindrical insert so that the irrigating fluid is channeled into the plurality of discrete circumferentially arranged distal channel sections 62. The fluid is directed from the distal tip as diagrammatically shown by arrow 63 in FIG. 2.

The cylindrical insert has an interior cylindrical bore which receives the inner member. The insert acts as a fluid seal and a bushing within which the inner member rotates and a similar, although unchanneled bushing 64 is situated at the proximal end of the outer member. Polymeric (or other suitable) tubular seals 70 are joined to the proximal and distal ends of the inner member (1) to provide a bearing function between the rotating inner member and the stationary cylindrical insert and (2) to provide a fluid seal to assure that irrigating fluid is directed properly through the distal channels. The distal seal 70 also assures that aspiration through aperture 24 acts primarily on material such as aspirated tissue debris and fluid at the surgical site rather than fluid in annular space 50. In the preferred embodiment seals 70 are shrink tubes made of Teflon.

As shown in FIG. 3, the circumferentially arranged distal channel sections 62 may be provided in a variety of designs. While all of the alternative inserts shown in FIG. 3 have cylindrical inner surfaces in order to rotatably receive the inner member, the external surfaces of the inserts may vary. As shown in FIG. 3a, the external surface of the insert may be formed into six longitudinally extending flats which, in cooperation with the inner surface of the outer tubular member, form a plurality of longitudinally extending channel sections 62 each having a transverse cross-section defined by a radially inward flat surface (on the cylindrical insert) and a radially outward arcuate surface (on the inner surface of the outer member). A similar arrangement is shown in FIG. 3b although the channel sections are formed with arcuate surfaces on both the radially inner and outer sides of the channel sections. As shown in FIG. 3c, the number of channel sections may be reduced to four sections which are shaped similarly to those shown in FIG. 3b. As shown in FIG. 3d, the channel sections may be made with different and smaller cross-sections more in the nature of semi-circular cross-sections. As shown in FIG. 3e, five channel sections may be used similar in shape to those shown in FIG. 3a. In FIG. 3f, four channel sections are shown similar in cross-section to those of FIG. 3e. As shown in FIG. 3g, the number of channel sections may be varied and repositioned so that the channel sections are not uniformly arranged around the exterior of the cylindrical insert. The arrangement shown in FIG. 3g will be understood to direct fluid from selected portions of the distal tip of the device. For example, referring to FIG. 2 and 3g, the fluid flow could be directed from the 9 o'clock, 12 o'clock and the 3 o'clock positions shown in FIG. 3g, these positions being proximally situated from the distal-most (6 o'clock) tip 72 of the angularly profiled outer tubular member. Varying the fluid flow in such a manner may facilitate fluid circulation in a desired pattern within or at the surgical work site.

Figure 7:
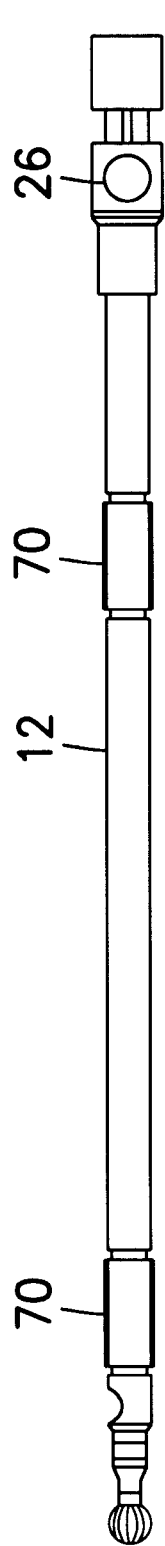
FIG. 7 is a side elevational view of the inner tubular member of the burr assembly of FIG. 1 showing a burr at its distal tip.
Figure 8:
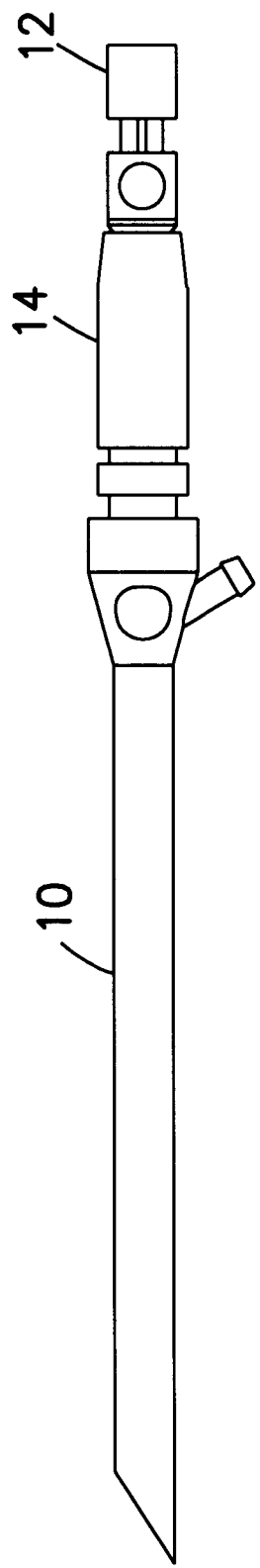
FIG. 8 is a side elevational view of an assembled irrigated burr assembly but not showing the distal tip of the burr extending beyond the distal tip of the outer tubular member.

As shown in FIGS. 4 through 8, the inner and outer tubular members comprise a plurality of elongated components which may be assembled using techniques well known to those skilled in the art. Outer member 14 comprises a hollow tube 76 having a port 30 and a knurled area 78. Tube 76 is assembled with cylindrical insert 60, hub 80, bushing/seal 82 and washer 84 and then may be attached to fluid adapter 40. Inner member 12 shown in FIG. 7 is then assembled with the components of FIG. 6 to produce the irrigated burr 10 of FIGS. 1 and 8.

Figure 9:
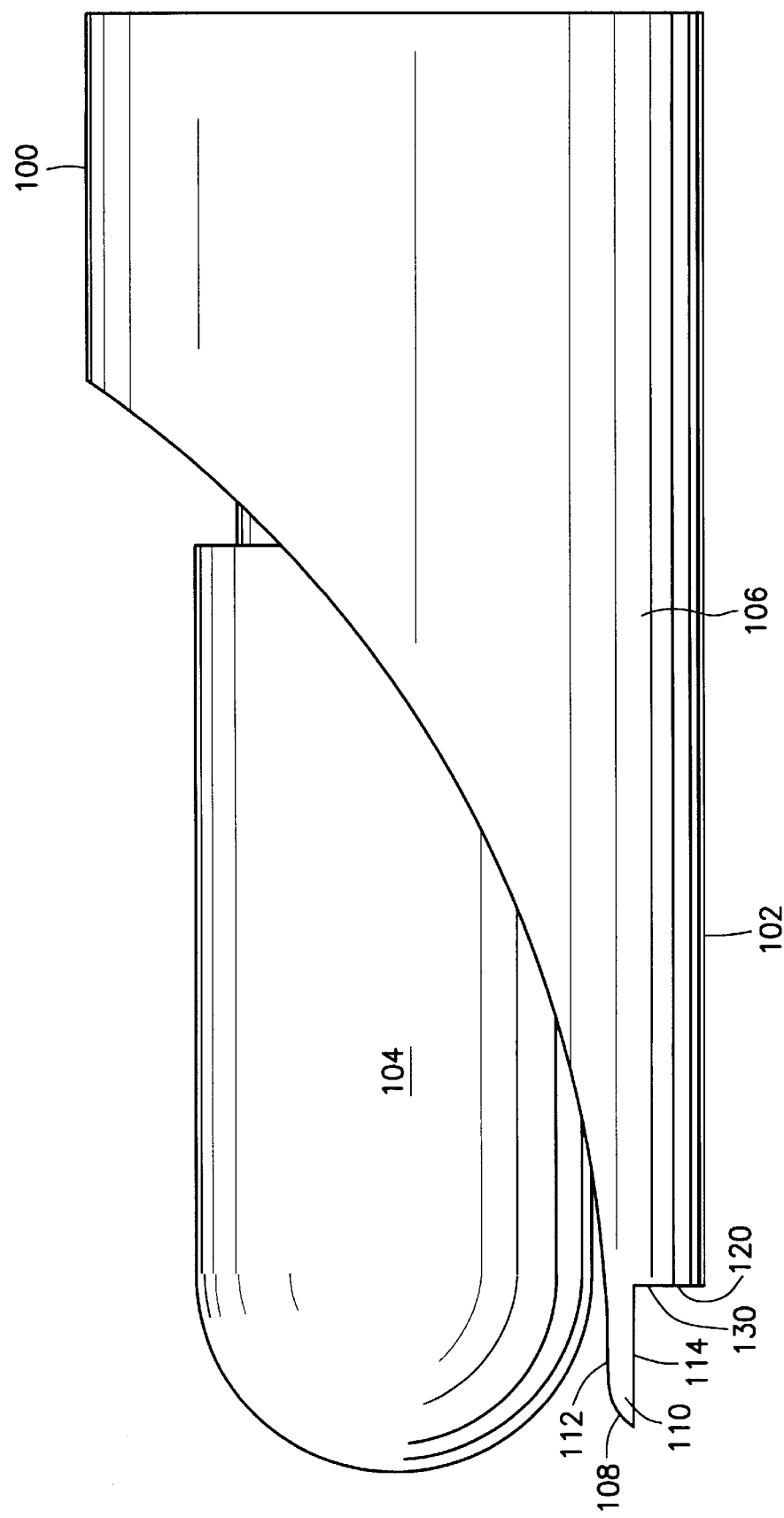
FIG. 9 is a side elevational view of an alternate embodiment of the distal tip of an irrigated burr assembly.
Figure 10:
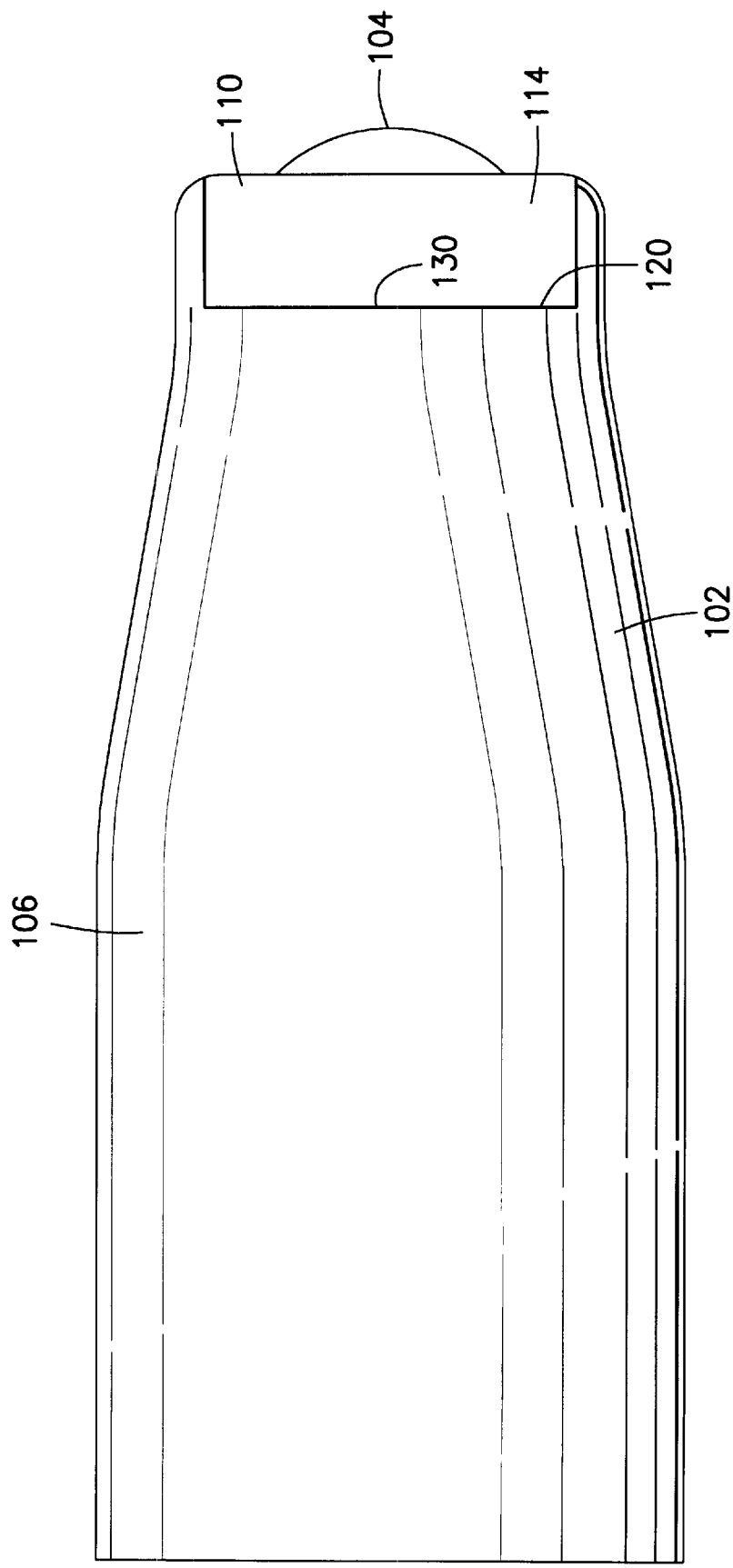
FIG. 10 is a bottom plan view of FIG. 9.
Figure 11:
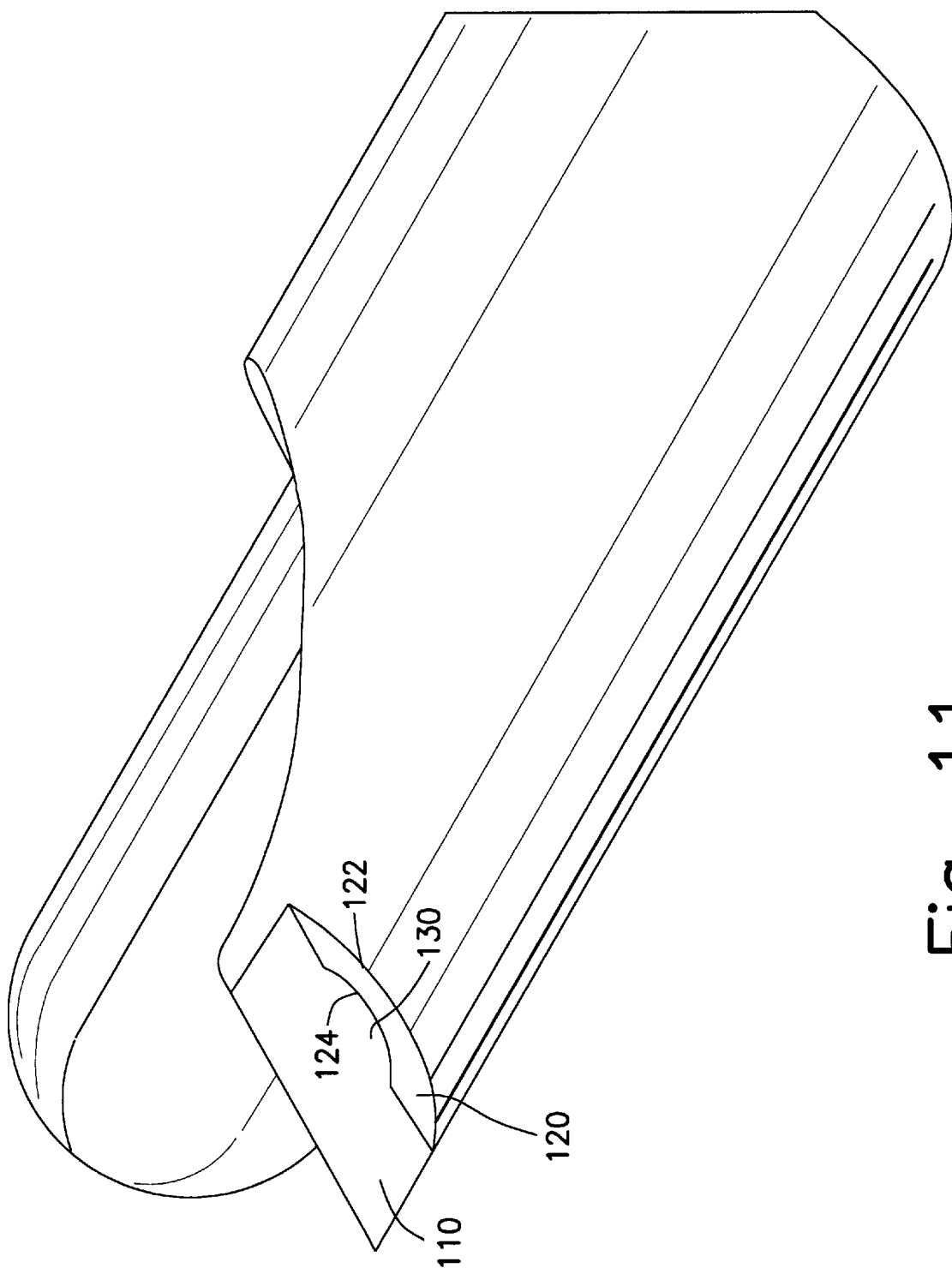
FIG. 11 is a bottom front perspective view of the device shown in FIG. 9.

As shown in FIG. 9, an alternate embodiment, shown as irrigated burr 100 may be provided with a distal tip 102 as shown. The proximal portions of burr 100 are similar to the proximal portions of irrigated burr 10 shown above. The burr 104 of this device may be a conventional burr tip analogous to burr 20 shown above. Outer tubular member 106 of burr 100 receives in its distal end a cylindrical insert which is provided at its distal-most end 108 with a longitudinally extending ledge 110 having a radially inwardly facing surface 112 and a radially outwardly facing surface 114. The distal end of the cylindrical insert and the distal end of the outer tube are secured together (by, for example, welding) so that the various parts all appear to be part of the outer tube. Ledge 110 extends distally from a transverse wall 120 which, as best seen in FIG. 11, has a radially outer edge 122, corresponding to the intersection of surface 120 with the outer surface of outer tube 106, and a radially inner edge 124, corresponding to the intersection of surface 120 with the inner surface of the outer tubular member 106. The space between surface 120 and ledge 110 defines a distal channel section 130, best seen in FIG. 11. In the embodiment shown in FIGS. 9–11, distal channel section 130 may be the only exit aperture for irrigating fluid from the distal tip of the burr. Said another way, with reference to the various distal channel section embodiments shown in FIG. 3, the embodiment of FIGS. 9–11 has a single distal channel section at the 6 o'clock position when viewed from the distal end of the irrigated burr assembly. Horizontal ledge 110 serves as a barrier and enables fluid to exit from channel section 130 without being immediately drawn back towards the aperture 22. Thus, ledge 110 enables the fluid to be directed and dispersed at the surgical work site so that it can effectively irrigate the site prior to being aspirated through aperture 22. The use of a single channel restricts fluid flow so that a somewhat forceful fluid stream may be provided. This fluid stream splashes the work site to improve visualization by cleaning the endoscope tip and clearing bone dust and other tissue debris from the area.

The invention may be adapted for use in bendable shaver blade assemblies or for use in burr guards used to protect surrounding tissue in open or closed surgical procedures. The irrigating fluid may be directed to cool various components and then directed as taught herein to irrigate the surgical site.

It will be understood by those skilled in the art that numerous improvements and modifications may be made to the preferred embodiment of the invention disclosed herein without departing from the spirit and scope thereof.

What is claimed is:

1. An elongated powered surgical resection instrument comprising:

an elongated outer member having a distal end, a proximal end and an axis;

an elongated inner member having a distal end, a proximal end and an axis and rotatably situated within said outer member;

a cutting element secured to said distal end of said inner member;

a fluid inlet port at said proximal end of said outer member;

at least one fluid outlet port at said distal end of said outer member, said fluid outlet port adapted to direct fluid distally;

a fluid channel means for communicating fluid from said fluid inlet port to said fluid outlet port;

a fluid blocking member interposed in said fluid channel means between said fluid inlet port and said at least one fluid outlet port for directing fluid to said at least one fluid outlet port; and seal means interposed between said inner and said fluid blocking member for preventing fluid passage therebetween.

2. An elongated powered surgical resection instrument according to claim 1 further comprising a transversely extending barrier member interposed between said fluid outlet port and said cutting element.

3. An irrigatable surgical instrument comprising:

an elongated tubular outer member having an axis, a proximal end, a distal end and an opening;

an elongated tubular inner member rotatably situated within said outer member and having an axis, a proximal end, a distal end, a tissue cutting means adjacent said opening and a lumen for aspirating material therethrough;

a fluid inlet port means in said outer member for directing fluid toward the distal end of said outer member;

channel means at said distal end of said outer member for receiving fluid from said fluid inlet port means, said channel means comprising a plurality of longitudinally aligned, annularly spaced channels for communicating fluid to the distal end of the outer member and directing fluid distally therefrom, each of said channels having a proximal end and a distal end and at least one of said channels having its distal-most, fluid outlet end situated distally of a portion of said tissue cutting means.

4. A surgical instrument according to claim 3 wherein said tissue cutting means is a burr.

5. A surgical instrument according to claim 3 wherein said channel means further comprises an axially aligned bore, fluidically isolated from said annularly spaced channels, for rotatably supporting said inner member.

6. An elongated powered surgical resection instrument according to claim 3 further comprising a transversely extending barrier member interposed between said fluid outlet port and said cutting element.

7. A method of resecting tissue at a non-fluid filled surgical site comprising the steps of:

providing an elongated powered cutting instrument having a proximal end, a distal end, a fluid inlet port at said proximal end and an aspiration port at said distal end;

providing said instrument with a cutting element having proximal and distal ends;

providing said instrument with a fluid outlet port adapted to direct fluid distally and situation said fluid outlet port distally of a portion of said cutting element;

providing said instrument with a fluid channel means for communicating fluid from said fluid inlet port to said fluid outlet port;

providing at the distal end of said instrument a fluid blocking member interposed in said fluid channel means between said fluid inlet port and said at least one fluid outlet port for directing fluid to said at least one fluid outlet port; and resecting tissue while directing fluid from said fluid outlet port.

8. A method according to claim 7 further comprising the step of:

providing a distally extending barrier wall means between said fluid outlet port and said aspiration port for preventing direct communication of fluid from said fluid outlet port to said aspiration port.

9. A method according to claim 7 wherein said instrument comprises:

an elongated tubular outer member having an axis, a proximal end, a distal end and an opening; an elongated tubular inner member rotatably situated within said outer member and having an axis, a proximal end, a distal end, a tissue cutting means adjacent said opening and a lumen for aspirating material therethrough.

* * * * *